United States Patent
Jochum, Jr.

(10) Patent No.: US 6,813,929 B2
(45) Date of Patent: Nov. 9, 2004

(54) METHOD AND APPARATUS FOR MONITORING FLUID FLOW

(75) Inventor: Peter S. Jochum, Jr., Seefeld (DE)

(73) Assignee: Dionex Corporation, Sunnyvale, CA (US)

(*) Notice: Subject to any disclaimer, the term of this patent is extended or adjusted under 35 U.S.C. 154(b) by 195 days.

(21) Appl. No.: 10/212,626

(22) Filed: Aug. 1, 2002

(65) Prior Publication Data

US 2004/0020308 A1 Feb. 5, 2004

(51) Int. Cl.[7] ............................................. G01N 30/36
(52) U.S. Cl. ..................................... 73/23.27; 73/23.41
(58) Field of Search .......................... 73/23.27, 23.41, 73/23.42, 23.24, 23.23

(56) References Cited

U.S. PATENT DOCUMENTS

| | | | |
|---|---|---|---|
| 3,800,593 A | * | 4/1974 | Bradley ..................... 73/23.27 |
| 4,123,236 A | * | 10/1978 | Hirschfeld et al. ........ 73/23.27 |
| 4,196,612 A | * | 4/1980 | Clardy et al. .............. 73/23.27 |
| 4,414,842 A | | 11/1983 | Small et al. |
| 5,089,126 A | | 2/1992 | Silebi et al. |
| 5,234,586 A | | 8/1993 | Afeyan et al. |
| 6,637,263 B2 | | 10/2003 | Zimmermann et al. |

FOREIGN PATENT DOCUMENTS

| | | |
|---|---|---|
| DE | 199 14 358 A1 | 10/2000 |
| EP | 0495255 B1 | 6/1996 |
| EP | 1 248 096 A1 | 10/2002 |

* cited by examiner

*Primary Examiner*—Harshad Patel
(74) *Attorney, Agent, or Firm*—Dorsey & Whitney LLP (57) ABSTRACT

An apparatus for monitoring fluid flow within a high pressure liquid chromatography system. The apparatus includes a pump for supplying a system flow of eluent to the system, a chromatography column, a flow splitting device having a first restrictor fluidly connecting the pump and the chromatography column, a second restrictor fluidly connecting the pump to a waste line, a first fluid pressure sensor monitoring a system fluid pressure upstream of the first restrictor, and a second fluid pressure sensor monitoring a column fluid pressure downstream of the first restrictor. A method of using the apparatus for fluid flow control is also disclosed.

24 Claims, 3 Drawing Sheets

METHOD AND APPARATUS FOR MONITORING FLUID FLOW

BACKGROUND OF THE INVENTION

1. Field of the Invention

This invention relates, in general, to a monitoring apparatus for a fluid flow system, such as a high pressure liquid chromatography system, and to methods for its use.

2. Description of Related Art

High pressure liquid chromatography (HPLC) generally requires the components of a sample to be separated or analyzed be dissolved in a mobile phase liquid, termed an eluent, and conveyed by that liquid to a stationary phase, that is, a chromatography column. HPLC eluent delivery systems are used to supply the liquid and deliver the liquid, with dissolved sample, to the column.

Specially designed HPLC pumps are used to deliver the liquid at precisely controlled flow rates in a smooth and uniform manner. In this manner, the composition of the eluent can be varied in controlled amounts whereby the strength of the mobile phase can be increased linearly or in increments in elution of the sample. This process is commonly referred to as gradient elution. During an HPLC gradient elution, the composition of the eluent is changed temporally to effect the elution of components in the sample with a wide range of affinities for the stationary phase.

As the composition or gradient profile of the eluent changes, the viscosity of the eluent also changes. For example, an eluent composed of water and methanol (MeOH) has the interesting property that the viscosity is actually at a maximum close to the point where the solvents, water and methanol, are nearly equally proportioned. Although water is more viscous than methanol, the maximum viscosity of an $H_2O$/MeOH gradient is not reached at 100% water, but at a mixing ratio of 60:40 of water to methanol. This viscosity maximum is about 60% higher than the viscosity of water alone.

Figure 1:
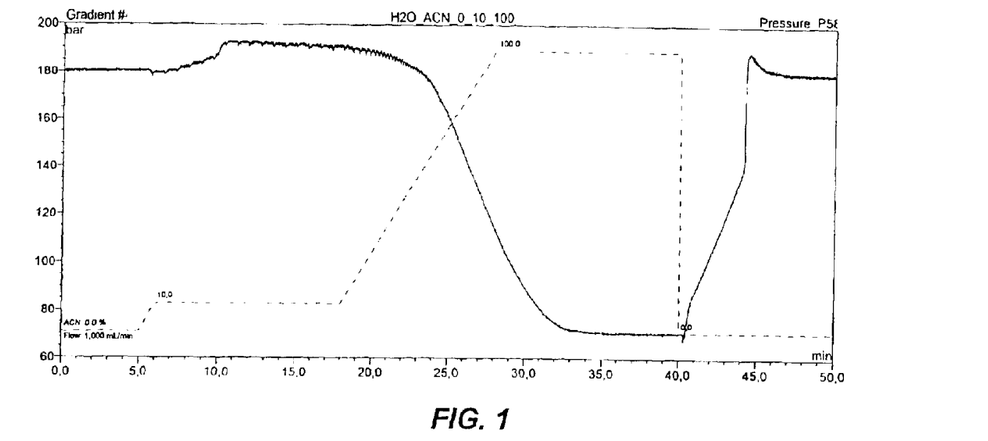
FIG. 1 is a graph illustrating the pressure profile of $H_2O$/ACN.

Water and acetonitrile (ACN) are also commonly used together as an eluent. The viscosity of water and acetonitrile differs by as much as 250%. However, the viscosity ratio of water and acetonitrile is similar to that of water and methanol. Thus running an $H_2O$/ACN gradient generates a S-shaped pressure profile rather then a constantly decreasing curve. The S-shaped $H_2O$/ACN pressure profile is shown in FIG. 1.

Micro-flow processors for varying the composition of the eluent are known. An exemplar of a prior art splitter is disclosed by European Patent No. EP 0 495 255 B1 to LC Packings, which patent shows a micro-flow processor having two restrictor portions which are formed by capillaries of different internal diameters and lengths. The flow splitter of the European '255 patent includes two capillaries with a solvent resistance ratio defined by the split ratio, e.g. 1:70.

Often, the method of splitting the flow by two capillaries whose length is proportional to the split ratio does not work in practice, because the back pressure within each capillary depends on the viscosity of the eluent. If the eluent composition differs in the two capillaries, the viscosity of the eluent differs and, thus, the splitting ratio varies as well.

Disadvantageously, the residence time of the gradient profile in the capillary coupled to the column must be similar to that of the gradient profile in the capillary coupled to a waste line in order for a flow splitter to function correctly when temporal eluent gradients are employed. Otherwise, hydraulic resistance of each capillary leg or restrictor portion will change at dissimilar rates and the flow rates through both capillary legs will change during the gradient development.

What is needed is a method and apparatus for monitoring the actual micro-flow through a flow splitter which overcomes the above and other disadvantages of known flow splitters.

BRIEF SUMMARY OF THE INVENTION

In summary, one aspect of the present invention is directed to an apparatus for monitoring flow within a high pressure liquid chromatography system, the apparatus including a pump for supplying a system flow of eluent to the system, a chromatography column, a flow splitting device including a first restrictor and a second restrictor, the first restrictor fluidly connecting the pump and the chromatography column and the second restrictor fluidly connecting the pump to a waste line, a first fluid pressure sensor monitoring a system fluid pressure upstream of the first restrictor, and a second fluid pressure sensor monitoring a column fluid pressure downstream of the first restrictor.

Preferably, the apparatus includes a supply line fluidly connecting the pump to the splitting device and a feed line fluidly connecting the first restrictor to the column. The first fluid pressure sensor coupled to the supply line for monitoring the system fluid pressure and the second fluid pressure sensor is coupled to the feed line for monitoring the column fluid pressure.

Preferably, in one embodiment, the apparatus further includes a calculating device for calculating a quotient Q based upon the system fluid pressure and the column fluid pressure as follows:

$$Q = P_{sys}/(P_{sys} - P_{col})$$

wherein $P_{sys}$ is the system fluid pressure and $P_{col}$ is the column fluid pressure.

Preferably, the apparatus includes a regulating device for regulating a required system flow necessary to provide a desired column flow based upon the system fluid pressure and the column fluid pressure.

In one embodiment, the apparatus includes a regulating device for regulating a required system flow $F_{sys}$ necessary to provide a desired column flow $F_{col}$ as follows:

$$F_{sys} = F_{col} \times (1+S) \times Q$$

wherein $F_{col}$ is the desired column flow, S is the split ratio of the flow splitting device, and Q is the quotient.

In another embodiment, the apparatus includes a regulating device for regulating a required system flow $F_{sys}$ necessary to provide a desired column flow $F_{col}$ as follows:

$$F_{sys} = F_{col} \times (1 + S \times Q)$$

wherein $F_{col}$ is the desired column flow, S is the split ratio of the flow splitting device, and Q is the quotient.

In yet another embodiment, the apparatus includes a regulating device for regulating a required system flow $F_{sys}$ necessary to provide a desired column flow $F_{col}$ as follows:

$$F_{sys} = F_{col} \times S \times Q$$

wherein $F_{col}$ is the desired column flow, S is the split ratio of the flow splitting device, and Q is the quotient.

Another aspect of the present invention is directed to an apparatus for monitoring flow within a high pressure liquid chromatography system, the apparatus including a pump for supplying a system flow of eluent to the system, a chromatography column, a flow splitting device including a first restrictor and a second restrictor, the first restrictor fluidly connecting the pump and the chromatography column and the second restrictor fluidly connecting the pump to a waste line, a first fluid pressure sensor monitoring a system fluid pressure upstream of the first restrictor, and a differential fluid pressure sensor monitoring a pressure differential between the system fluid pressure and a column fluid pressure downstream of the first restrictor.

Preferably, in another embodiment, the apparatus further includes a calculating device for calculating a quotient Q based upon the system fluid pressure and the pressure differential as follows:

$$Q=P_{sys}/P_{diff}$$

wherein $P_{sys}$ is the system fluid pressure and $P_{diff}$ is the pressure differential.

In one embodiment, the apparatus includes a regulating device for regulating a required system flow $F_{sys}$ necessary to provide a desired column flow $F_{col}$ as follows:

$$F_{sys}=F_{col}\times(1+S)\times Q$$

wherein $F_{col}$ is the desired column flow, S is the split ratio of the flow splitting device, and Q is the quotient.

In one embodiment, the apparatus includes a regulating device for regulating a required system flow $F_{sys}$ necessary to provide a desired column flow $F_{col}$ as follows:

$$F_{sys}=F_{col}\times(1+S\times Q)$$

wherein $F_{col}$ is the desired column flow, S is the split ratio of the flow splitting device, and Q is the quotient.

In one embodiment, the apparatus includes a regulating device for regulating a required system flow $F_{sys}$ necessary to provide a desired column flow $F_{col}$ as follows:

$$F_{sys}=F_{col}\times S\times Q$$

wherein $F_{col}$ is the desired column flow, S is the split ratio of the flow splitting device, and Q is the quotient.

Yet another aspect of the present invention is directed to a method for regulating a desired column flow within a high pressure liquid chromatography system including the steps of supplying an eluent via a supply line to a flow splitting device at a system flow rate, distributing the eluent from the splitting device via a feed line to a chromatography column, monitoring a system fluid pressure in the supply line, monitoring a column fluid pressure in the feed line, and calculating a quotient Q based upon the system fluid pressure and the column fluid pressure.

In one embodiment, the calculating step is accomplished by calculating the quotient Q as follows:

$$Q=P_{sys}/(P_{sys}-P_{col})$$

wherein $P_{sys}$ is the system fluid pressure and $P_{col}$ is the column fluid pressure.

In another embodiment, the calculating step is accomplished by calculating the quotient Q as follows:

$$Q=P_{sys}/P_{diff}$$

wherein $P_{sys}$ is the system fluid pressure and $P_{diff}$ is the differential pressure between the system fluid pressure and the column fluid pressure.

Preferably, the method includes the step of regulating a required system flow based upon quotient Q.

In one embodiment, the regulating step is accomplished by regulating the required system flow $F_{sys}$ as follows:

$$F_{sys}=F_{col}\times(1+S)\times Q$$

wherein $F_{col}$ is the desired column flow, S is the split ratio of the flow splitting device, and Q is the quotient.

In another embodiment, the regulating step is accomplished by regulating the required system flow $F_{sys}$ as follows:

$$F_{sys}=F_{col}\times(1+S\times Q)$$

wherein $F_{col}$ is the desired column flow, S is the split ratio of the flow splitting device, and Q is the quotient.

In yet another embodiment, the regulating step is accomplished by regulating the required system flow $F_{sys}$ as follows:

$$F_{sys}=F_{col}\times S\times Q$$

wherein $F_{col}$ is the desired column flow, S is the split ratio of the flow splitting device, and Q is the quotient.

Preferably, the method includes the step of adjusting the system flow rate to provide the desired column flow rate.

An object of the present invention is to provide a method and apparatus for monitoring the actual micro-flow through a splitter device of a fluid flow system.

Another object of the present invention is to provide a method and apparatus for monitoring actual micro-flow in order to minimize flow rate fluctuations in the fluid flow system.

Yet another object of the present invention is to provide a method and apparatus for monitoring the micro-flow of a mobile phase through a splitter device and to a stationary phase of an HPLC system with acceptable accuracy at any interval of time.

The method and apparatus for fluid flow control of the present invention has other features and advantages which will be apparent from or are set forth in more detail in the accompanying drawings, which are incorporated in and form a part of this specification, and the following Detailed Description of the Invention, which together serve to explain the principles of the present invention.

DETAILED DESCRIPTION OF THE INVENTION

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications and equivalents, which may be included within the spirit and scope of the invention as defined by the appended claims.

Figure 2:
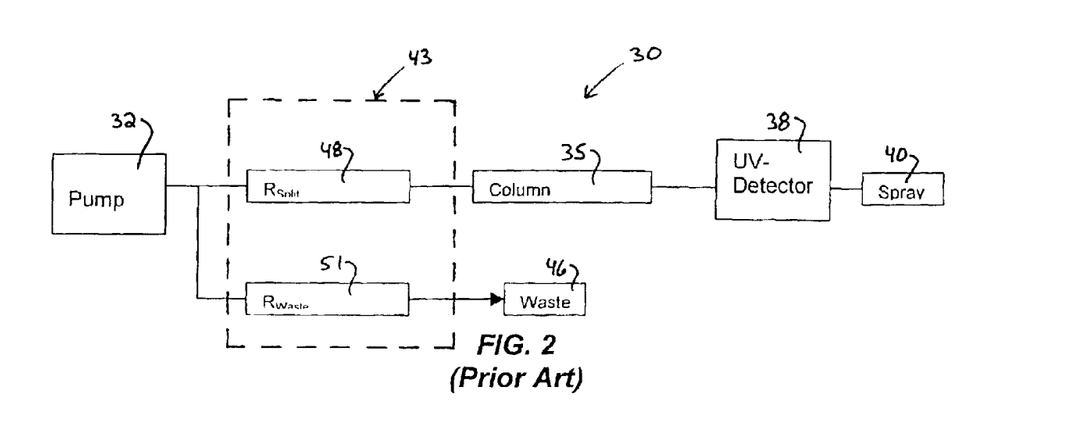
FIG. 2 is a schematic view of a prior art apparatus for fluid control.

Turning now to the drawings, wherein like components are designated by like reference numerals throughout the various figures, attention is directed to FIG. 2 which schematically illustrates a known fluid flow system 30 of the type utilized by the UltiMate™ Micro Pump and Detection Module currently sold by Dionex Corp. of San Francisco, Calif. As shown in FIG. 2, fluid flow system 30 includes a high pressure liquid chromatography (HPLC) pump 32 for supplying a flow of eluent to a liquid chromatography column 35, and in turn, an ultraviolet (UV) detector 38 and an electro-spray unit 40 for analysis in a conventional manner. Although the illustrated fluid flow system 30 includes a UV detector and an electro-spray unit, one should appreciate that the fluid flow system need not include such components. Alternatively, one should appreciate that the fluid flow system of the present invention may include these and other components known in the HPLC field.

Fluid flow system 30 is provided with a splitting device or splitter 43 for distributing eluent between column 35 and a waste line 46 at a predetermined split ratio S. Splitter 43 includes a first column restrictor or column branch 48 in fluid communication with column 35 and a second waste restrictor or waste branch 51 in fluid communication with waste line 46. One should appreciate that the eluent diverted to waste line 46 may be disposed of, stored in a reservoir, and/or, in applications other than gradient runs, recycled for reuse.

Column branch 48 is a high resistance branch which is formed by a capillary restrictor having a relatively small internal diameter. For the purpose of the discussion below, the first column restrictor or column branch 48 may also be referred to as a column capillary 48. Waste branch 51 is a low resistance branch which is formed by a capillary having a relatively large internal diameter, that is, one that is larger than the internal diameter of the column branch 48. For the purpose of the discussion below, the second waste restrictor or waste branch 51 may also be referred to as a waste capillary 51. Preferably, the capillary restrictors are of the type disclosed by European Patent No. EP 0 495 255 B1 to LC Packings, the entire contents of which is incorporated herein by this reference. One should appreciate, however, that the particular dimensions of the capillary restrictors, including the internal diameters and the lengths thereof, may vary in accordance with the present invention.

The split ratio S of splitter 43 is determined by the respective resistances ($R_{col}$ and $R_{waste}$) of column capillary 48 and waste capillary 51. For example, the split ratio can be determined by the following equation:

$$S = R_{col}/R_{waste} \quad \text{Eq. (a)}$$

where

S is the split ratio, $R_{col}$ is the resistance of column branch 48, and $R_{waste}$ is the resistance of waste capillary 51.

As can be seen in FIG. 2, a micro-flow ($\mu$-flow) of eluent, that is, a flow of eluent on the order of $\mu$l/min passes through fluid flow system 30 along a high resistance path which extends not only through column capillary 48 but also through the succeeding column 35, UV detector 38, and in many cases, electro-spray unit 40. Thus the actual $\mu$-flow into column 35 is dependent upon the resistance of column capillary 48 ($R_{col}$) in addition to the resistance of column 35 ($R_{column}$), detector 38 ($R_{detector}$) and spray 40 ($R_{spray}$). As a consequence, the $\mu$-flow is not determined by the specified split ratio S of splitter 43 alone.

For example, in typical columns and applications offered by Dionex Corp. the column back pressure is about one third of the system fluid pressure generated by the pump. If a 100:1 splitter is utilized in such a typical column and application, the actual split ratio would be approximately 150:1. Disadvantageously, such undesired effects on the actual split ratio increase substantially as resistance $R_{column}$ of the column increases as compared to resistance $R_{col}$ of the column capillary. Nor is the $\mu$-flow constant if the solvent viscosity changes. If solvent viscosity changes, the split ratio also changes as does the $\mu$-flow.

These undesired effects of prior systems are illustrated in the following example in which the following variables were used:

| | |
|---|---|
| Pump flow $F_{sys}$: | 200 $\mu$l/min |
| Solvent: | Water |
| Split ratio S: | 100:1 |
| Volume $R_{waste}$: | 100 $\mu$l (splitter delay volume) |
| Pump pressure $P_{sys}$: | 250 bar |
| Column pressure $P_{col}$: | 100 bar |

Although the expected column flow under the above conditions, assuming a 100:1 split ratio, is approximately 2 $\mu$l/min the actual column flow varies significantly. Using the above exemplary variables, the actual starting column flow $F_{col}$ has been determined as:

$$F_{col}(t=0) = 200 \times 0.01 \times 150/250 = 1.2 \; \mu l/min \quad \text{Eq. (b)}$$

Hence the actual starting $\mu$-flow of 1.2 $\mu$l/min is only approximately 60% of the expected flow of 2 $\mu$l/min.

Assuming that a step gradient from 100% $H_2O$ to 100% ACN is run, after approximately 30 seconds, both column branch 48 and waste capillary 51 are completely filled with ACN while the column is still filled with $H_2O$. At this time both splitter resistances $R_{col}$ and $R_{waste}$ are reduced by a factor of 2.5 due to ACN's much lower viscosity. The pump pressure decreases to 100 bar and the column flow $F_{col}$ is:

$$F_{col}(t=30 \; sec) = 200 \times 0.01 \times 60/160 = 0.75 \; \mu l/min \quad \text{Eq. (c)}$$

Hence the actual $\mu$-flow at the 30 second mark is approximately 0.75 $\mu$l/min which is only 38% of the expected flow of 2 $\mu$l/min.

Furthermore, the resulting actual column flow of 0.75 $\mu$l/min is only approximately 63% of the starting flow. In other words, the actual split ratio has increased to 267:1. As the gradient continues, the water in the column is displaced by ACN and the capillary flow returns to the starting flow conditions of 1.2 $\mu$l/min.

In view of the above trial, running a $H_2O$/ACN step gradient under the above conditions leads to a parabolic $\mu$-flow profile with an actual starting and ending column flow of approximately 60% of the desired column flow and an actual middle column flow at the 30 second mark of approximately 38% of the column flow that would be expected with a split ratio of 100:1.

It is worth noting that the above calculations utilize ideal conditions. One should appreciate that other physical effects may have an adverse effect on flow and thus retention stability. Firstly, few physical parameters are as temperature dependent as viscosity. While this has no impact on the splitter's resistance ratio S as long as both the column and waste capillaries are kept at the same temperature, the actual split ratio S is seriously influenced by the back pressure of the splitter and the back pressure of the column. With varying column temperature the column back pressure changes and so does the split ratio S which, in turn, leads to a considerable difference in the actual $\mu$-flow to the column.

Secondly, the column back pressure of aging columns typically increases. The column back pressure may increase up to and/or in excess of approximately 100% at the end of a column's life. For simple pumps having a back pressure dependent flow, for example, pumps with pulse dampers and/or bad compressibility compensation, it is well-known that peaks "wander out" with aging columns. In the above example, if the column back pressure doubled, the corresponding $\mu$-flow to the column would be reduced to 0.86 $\mu$l/min or to 71% of the flow of a new column. As a consequence, the peak retention times would increase by as much as 40% compared to the performance of a new column.

In analytical scale HPLC, both effects are compensated to a large extent by a good pump. HPLC pumps are measured by their ability to deliver an accurate and constant flow independent of solvent type, viscosity, solvent compressibility, and column age. A good analytical scale HPLC pump generally has tolerances which allow for a maximum of 3% flow variation by back pressure, viscosity, and compressibility. As can be seen above, however, the actual flow rates through fluid flow system 30 may exceed the 3% tolerances by more than an order of magnitude even if pump 32 is perfectly accurate and precise, which is generally not the case.

Figure 3:
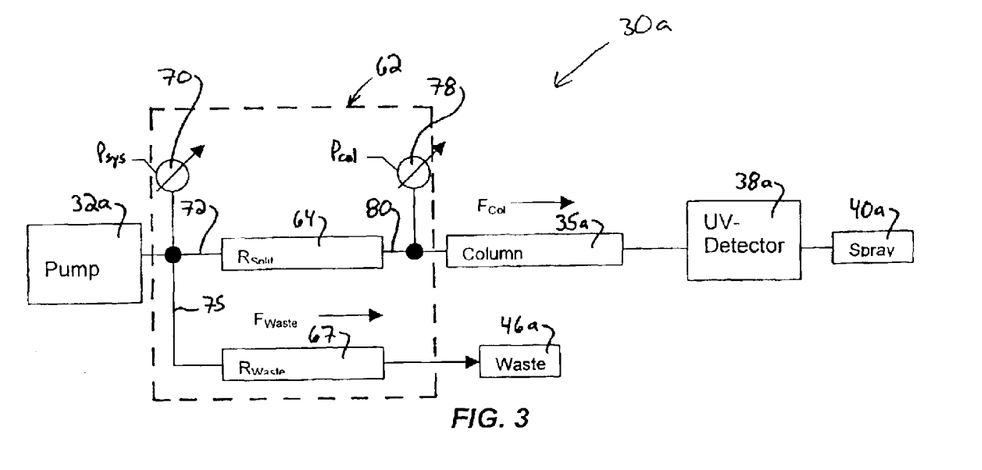
FIG. 3 is a schematic view of an apparatus for fluid control in accordance with the present invention.

Turning now to FIG. 3, a new and improved fluid flow system 30a in accordance with the present invention is provided with an improved flow control apparatus 62 in order to overcome the disadvantages of known fluid flow systems. In particular, flow control apparatus 62 of system 30a is configured to monitor the actual $\mu$-flow traveling through the system and into column 35a.

FIG. 3 schematically illustrates fluid flow system 30a which includes an HPLC pump 32a for supplying an eluent to a liquid chromatography column 35a, and in turn, a UV detector 38a and an electro-spray unit 40a in a manner similar to that discussed above. Similar to system 30 above, fluid flow system 30a need not include a UV detector and/or an electro spray unit in order to operate in accordance with the present invention. Alternatively, one should appreciate that the fluid flow system of the present invention may include other types of detectors and/or analytical components in addition to, or instead of, the UV detector and the electrospray unit.

Similar to system 30 above, fluid flow system 30a is provided with a flow control apparatus or splitter 62 for distributing eluent between column 35a and a waste line 46a. Unlike system 30 above, however, fluid flow system 30a is capable of monitoring a system fluid pressure upstream from splitter 62 and a column fluid pressure downstream from splitter 62.

Splitter 62 includes a first column capillary or restrictor 64 in fluid communication with column 35a and a second waste capillary or restrictor 67 in fluid communication with waste line 46a. Splitter 62 is configured not only to distribute eluent between column 35a and waste line 46a at a predetermined split ratio S, but is also configured to allow for compensation of the varying split ratio by adjusting the pump flow.

The first restrictor or column capillary 64 is a high resistance branch which is formed by a capillary restrictor having a relatively high fluid resistance. The second restrictor or waste capillary 67 is a low resistance branch which is formed by a capillary having a relatively flow fluid resistance, that is, one that is lower than that of the column capillary 64. Again, the capillary restrictors preferably are of the type disclosed by European Patent No. EP 0 495 255 B1 to LC Packings, the entire contents of which is incorporated herein by this reference. One should appreciate, however, that the particular dimensions of the capillary restrictors, including the internal diameters and the lengths thereof, may vary in accordance with the present invention.

For example, with reference to the above example, had the $\mu$-flow from pump been increased from 200 $\mu$l/min to approximately 539 $\mu$l/min at the time, where the column capillary is filled with ACN and the column is filled with water, that is, at the 30 second mark, the column flow would have remained at approximately 1.2 $\mu$l/min instead of dropping down to 0.75 $\mu$l/min. Thus, by monitoring pressure in accordance with the present invention, the system flow $F_{sys}$ of the pump can be regulated in order to provide a desired column flow at any moment in time. Furthermore, by monitoring pressure in accordance with the present invention, flow control apparatus 62 can monitor the true $\mu$-flow through the system and into the column with acceptable accuracy at any time.

In accordance with the present invention, flow control apparatus 62 includes a first pressure sensor 70 located before column capillary 64 and waste capillary 67 for measuring the system fluid pressure before the split. In the illustrated embodiment, an eluent supply line 72 fluidly connects pump 32a with high resistance column capillary 64 and the system fluid pressure sensor 70 is located in supply line 72 upstream from column capillary 64. System pressure sensor 70 may be located at the intersection of eluent supply line 72 and a waste line 75 which is in fluid communication with low resistance waste capillary 67. Alternatively, the system fluid pressure sensor can be located internal to the pump in such a manner that the system fluid pressure sensor is in fluid communication with the eluent supply line.

Flow control apparatus also includes a second pressure sensor 78 located after column capillary 64 and before column 35a for measuring the column fluid pressure after the split. In the illustrated embodiment, an eluent feed line 80 fluidly connects high resistance column capillary 64 with column 35a. Column pressure sensor 78 is located in feed line 80 downstream from column capillary 64.

Calibration of the two pressure sensors allows monitoring of the pressure drop through column capillary 64 with high accuracy. With reference to FIG. 3, system fluid pressure sensor 70 monitors system fluid pressure $F_{sys}$ before the splitter and column fluid pressure sensor 78 monitors column fluid pressure $P_{col}$ after the splitter. From the monitored system and column fluid pressures, a system flow ($F_{sys}$) relative to a column flow ($F_{col}$) can be determined in accordance with the present invention. In particular, the monitored pressures can be used to determine the actual column flow based upon a predetermined system flow, that is, pumped flow can be determined. Alternatively, the monitored pressures can be used to determine a required system flow to maintain a desired column flow.

System flow can be determined as follows:

$$F_{sys}=F_{col}+F_{waste}=F_{col}+P_{sys}/R_{waste} \qquad \text{Eq. (d)}$$

where $F_{sys}$ is the system flow delivered by the pump, $F_{col}$ is the column flow through the column capillary and into the column, $F_{waste}$ is the waste flow through the waste capillary and to the waste line, $P_{sys}$ is the system fluid pressure upstream from the column capillary, and $R_{waste}$ is the is the resistance of the waste capillary.

By utilizing the fluid dynamic analogy of Ohm's law, the system fluid pressure $P_{sys}$ can be factored as follows:

$$P_{sys} = F_{col} \times R_{col} + P_{col} \qquad \text{Eq. (e)}$$

where $P_{sys}$ is the system fluid pressure upstream from the column capillary, $F_{col}$ is the column flow through the column capillary and into the column, $R_{col}$ is the resistance of the column capillary, and $P_{col}$ is the column fluid pressure downstream from the column capillary.

Inserting equation (e) in equation (d) yields:

$$\begin{aligned} F_{sys} &= F_{col} + (F_{col} \times R_{col} + P_{col})/R_{waste} \qquad \text{Eq. (f)} \\ &= F_{col} + F_{col} \times R_{col}/R_{waste} + P_{col}/R_{waste} \end{aligned}$$

Although both $R_{col}$ and $R_{waste}$ vary with viscosity, $R_{col}/R_{waste}$ may be replaced by split ratio S provided that the resistance ratio remains constant. For example, the resistance ratio may be held constant with a splitter of the type disclosed by European Patent No. EP 0,495,255 B1. The design of such a splitter relies on the internal diameter dimensions of the column and the split capillaries. Accordingly, system flow $F_{sys}$ can be determined as follows:

$$\begin{aligned} F_{sys} &= F_{col} + F_{col} \times S + P_{col}/R_{waste} \qquad \text{Eq. (g)} \\ &= F_{col} \times (1 + S) + P_{col}/R_{waste} \end{aligned}$$

wherein S is the split ratio of the splitter.

Assuming column flow $F_{col}$ is the desired μ-flow into the column as desired by a laboratory technician or other user, the primary system flow $F_{sys}$ can be adjusted in accordance with the present invention to generate and maintain the desired column flow $F_{col}$, provided that column fluid pressure $P_{col}$ and the resistance of the waste capillary $R_{waste}$ are known. As noted above, column fluid pressure sensor 78 monitors column fluid pressure $P_{col}$. The remaining variable, the resistance of the waste capillary $R_{waste}$ can be approximated as follows:

$$R_{waste} = P_{sys}/F_{waste} \qquad \text{Eq. (h)}$$

As the waste flow $F_{waste}$ is substantially larger than the column flow $F_{col}$ the waste flow $F_{waste}$ can be substituted with $F_{sys}$. Provided that the split ratio is greater than 99:1, the resulting error is less than 1%.

By inserting equation (h) into equation (g) and replacing $F_{waste}$ by $F_{sys}$ the system flow $F_{sys}$ can be approximated as follows:

$$\begin{aligned} F_{sys} &= F_{col} \times (1 + S) + P_{col}/R_{waste} \qquad \text{Eq. (i)} \\ &= F_{col} \times (1 + S) + (P_{col}/P_{sys}) \times F_{waste} \\ &\approx F_{col} \times (1 + S) + (P_{col}/P_{sys}) \times F_{sys} \end{aligned}$$

Solving for system flow $F_{sys}$ eventually yields:

$$F_{sys} = F_{col} \times (1+S) \times P_{sys}/(P_{sys} - P_{col}) \qquad \text{Eq. (j)}$$

If $F_{waste}$ is replaced by its exact definition $F_{waste} = F_{sys} - F_{col}$ the following equation is obtained:

$$\begin{aligned} F_{Sys} &= F_{Col} \times (1 + S) + (P_{col}/P_{sys}) \times F_{waste} \qquad \text{Eq. (k)} \\ &= F_{col} \times (1 + S) + (P_{col}/P_{sys}) \times (F_{sys} - F_{col}) \end{aligned}$$

Solving for system flow $F_{sys}$ now leads to a slightly different formula:

$$\begin{aligned} F_{sys} &= F_{col} \times [(1 + S) \times P_{sys} - P_{col}]/(P_{sys} - P_{col}) \qquad \text{Eq. (l)} \\ &= F_{col} \times [1 + S \times P_{sys}/(P_{sys} - P_{col})] \end{aligned}$$

Both equations (j) and (q) contain the quotient $P_{sys}/(P_{sys} - P_{col})$. As the system and column fluid pressures $P_{sys}$ and $P_{col}$ are monitored by system and column fluid pressure sensors 70 and 78, respectively, this quotient Q can be determined as follows:

$$Q = P_{sys}/(P_{sys} - P_{col}) \qquad \text{Eq. (m)}$$

Although neither the system fluid pressure $P_{sys}$ nor the column fluid pressure $P_{col}$ are known for the target flow $F_{sys}$ the quotient Q remains the same for all flows at a given time. This is due to the fact that at any time the resistances obey Ohm's law, which in fluid dynamics is normally called the Hagen-Poiseuille relationship (see, for example, European Patent No. EP 0 495,255). Of course, Q changes with time due to viscosity changes in a strongly nonlinear manner, but at any given time, both $P_{sys}$ and $P_{col}$ linearly depend on flow. For example, if the system flow was doubled at a given time, both $P_{sys}$ and $P_{col}$ would double leaving the quotient Q unchanged. Thus Q depends on time only.

It should also be observed that normally S>>1 and Q>1 since Q can be rewritten as:

$$\begin{aligned} Q &= (P_{sys} - P_{col} + P_{col})/(P_{sys} - P_{col}) \qquad \text{Eq. (n)} \\ &= 1 + P_{col}/(P_{sys} - P_{col}) > 1 \end{aligned}$$

Thus, S×Q>>1. As a consequence, equations (j) and (l) imply that the following three relationships deliver virtually the same results, if the split ratio S is large:

$$F_{sys} = F_{col} \times (1+S) \times Q \qquad \text{Eq. (o)}$$

$$F_{sys} = F_{col} \times (1+S \times Q) \qquad \text{Eq. (p)}$$

$$F_{sys} = F_{col} \times S \times Q \qquad \text{Eq. (q)}$$

Thus, in order to determine the required system flow $F_{sys}$ for a desired column flow $F_{col}$, one would simply need to monitor the current pressure values read by the system and column fluid pressure sensors and adjust the system flow by evaluating one of the equations (o), (p), or (q). For simplicity, we restrict our considerations in the following to the application of equation (p) being the most precise one.

The above method of pressure monitoring flow control can alleviate the undesired effects of prior systems. In particular, a constant column flow can be achieved as is shown in the following example which utilizes the following variables:

| | |
|---|---|
| Desired column flow $F_{col}$: | 2 μl |
| Split ratio S: | 100:1 |
| Pump pressure $P_{sys}$: | 250 bar |
| Column pressure $P_{col}$: | 100 bar |

In order to achieve a desired starting column flow of 2 μl/min, when only water is flowing through the splitter, the system flow $F_{sys}$ can be adjusted as follows:

$$F_{sys}=F_{col}\times(1+S\times P_{sys}/(P_{sys}-P_{col})) \quad \text{Eq. (r)}$$

$$F_{sys}=2 \text{ μl/min}\times(1+100\times250 \text{ bar}/(250 \text{ bar}-100 \text{ bar}))$$

$$F_{sys}=335 \text{ μl/min}$$

Accordingly, to maintain a starting column flow of 2 μl, the pump must be adjusted to provide solvent at a rate of 335 μl/min instead of 200 μl/min.

Again assuming that a step gradient from 100% H2O to 100% ACN is run, after approximately 30 seconds, i.e., in the middle of the run, both column capillaries are filled with ACN while the column is still filled with H2O. In this example, the system fluid pressure is 100 bar. Accordingly, the system flow can be adjusted to maintain the desired column flow of 2 μl/min as follows:

$$F_{sys}=F_{col}\times(1+S\times P_{sys}/(P_{sys}-P_{col})) \quad \text{Eq. (s)}$$

$$F_{sys}=2 \text{ μl/min}\times(1+100\times100 \text{ bar}/(100 \text{ bar}-62.5 \text{ bar}))$$

$$F_{sys}=535 \text{ μl/min}$$

Accordingly, to maintain an intermediate column flow $F_{col}$ of 2 μl at this point in time, the pump can be adjusted to provide solvent at a system flow rate $F_{sys}$ of 535 μl/min instead of 200 μl/min in order to provide a desired column flow rate $F_{col}$ of 2 μl/min.

One should appreciate that the flow control apparatus of the present invention can be provided with a calculating device and a regulating device in order to automatically regulate required system flow in order to provide a desired column flow.

Figure 4:
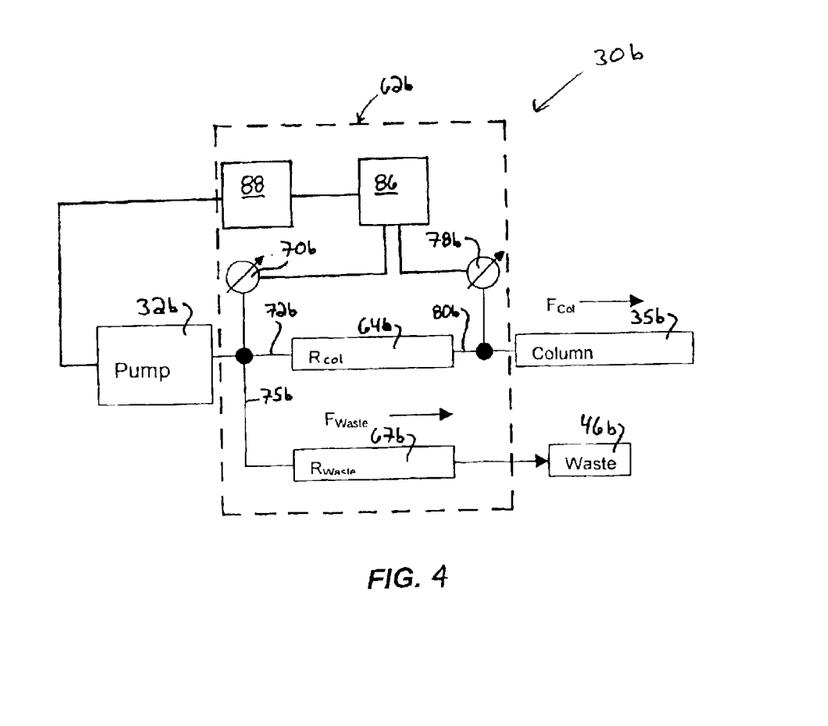
FIG. 4 is a schematic view of another apparatus for fluid control in accordance with the present invention.

As shown in FIG. 4, fluid flow system 30b includes a modified flow control apparatus 62b similar to apparatus 62 described above. However, flow control apparatus 62b is provided with a calculating device 86 and a regulating device 88 for automatically regulating the system flow in order to provide a desired column flow.

Generally, a software application is used to collect and analyze data corresponding to system fluid pressure $P_{sys}$ and column fluid pressure $P_{col}$. In particular, calculating device 86 operating such a software application is electrically coupled to system fluid pressure sensor 70b and column fluid pressure sensor 78b as shown in FIG. 4. Algorithms utilized by the software application calculate quotient Q in the same manner as discussed above. Once quotient Q is calculated, the software application can calculate either the actual column flow $F_{col}$ based upon the actual system flow $F_{sys}$, or the required system flow $F_{sys}$ based upon a desired column flow $F_{col}$.

One should appreciate that the software application need not be configured to calculate Q but may instead be configured such that it can determine either an actual column flow $F_{col}$ based upon the actual system flow $F_{sys}$ in combination with the measured system and column fluid pressures $P_{sys}$ and $P_{col}$, or a required system flow $F_{sys}$ based upon the desired column flow $F_{col}$, as set by the laboratory technician or other operator, in combination with the measured system and column fluid pressures $P_{sys}$ and $P_{col}$.

In the embodiment illustrated in FIG. 4, flow control apparatus 62b is provided with a regulating device or pump controller 88 which is capable of adjusting the system flow $F_{sys}$ delivered by HPLC pump 32b. In this embodiment, calculating device 86 determines a required system flow $F_{sys}$ based upon the desired column flow $F_{col}$, as set by the operator, in combination with the measured system and column fluid pressures $P_{sys}$ and $P_{col}$ as sensed by system fluid pressure sensor 70b and column fluid pressure sensor 78b. Calculating device 86 issues a corresponding controlling signal to pump controller 88 which, in turn, regulates operation of pump 32b in order to deliver the required system flow $F_{sys}$ at any time during a gradient run. One should appreciate that calculating device 86 and pump controller 88 can be configured to continuously monitor system and column fluid pressures during a gradient run such that it can continuously regulate pump 32b to provide the required system flow $F_{sys}$ necessary to provide a constant column flow $F_{col}$ to column 35b.

Advantageously, the method and apparatus of the present invention allows one to regulate the supply pump to deliver the required varying system flow $F_{sys}$ necessary to provide a constant, non-fluctuating column flow $F_{col}$ to the chromatography column. A constant flow is important for many reasons, including those discussed below.

In chromatography, the peak area is proportional to the amount of a separated component only if the flow is constant. Thus in order to precisely quantify the separated peaks, the flow should have as little fluctuation as possible.

For various detection devices such as UV detectors, a varying flow can lead to a shifting baseline, which makes peak integration harder.

Both retention time reproducibility and accuracy of the chromatographic peaks highly depend on a constant flow. Solvent viscosity is extremely temperature dependent and thus are the implied splitter and column resistances. As a consequence, the flow would typically vary with temperature. Thus keeping the flow constant by the above teaching reduces the temperature dependence of retention times to a minimum.

Since without the above teaching the flow depends on column resistance, the retention time of peaks increases with aging columns: "Peaks wander out". Controlling the system flow and thus keeping the μ-flow constant extends the column's life time and allows for a much larger number of analyses.

Advantageously, the performance of electro-spray LC-MS interfaces improves with constant flow.

Figure 5:
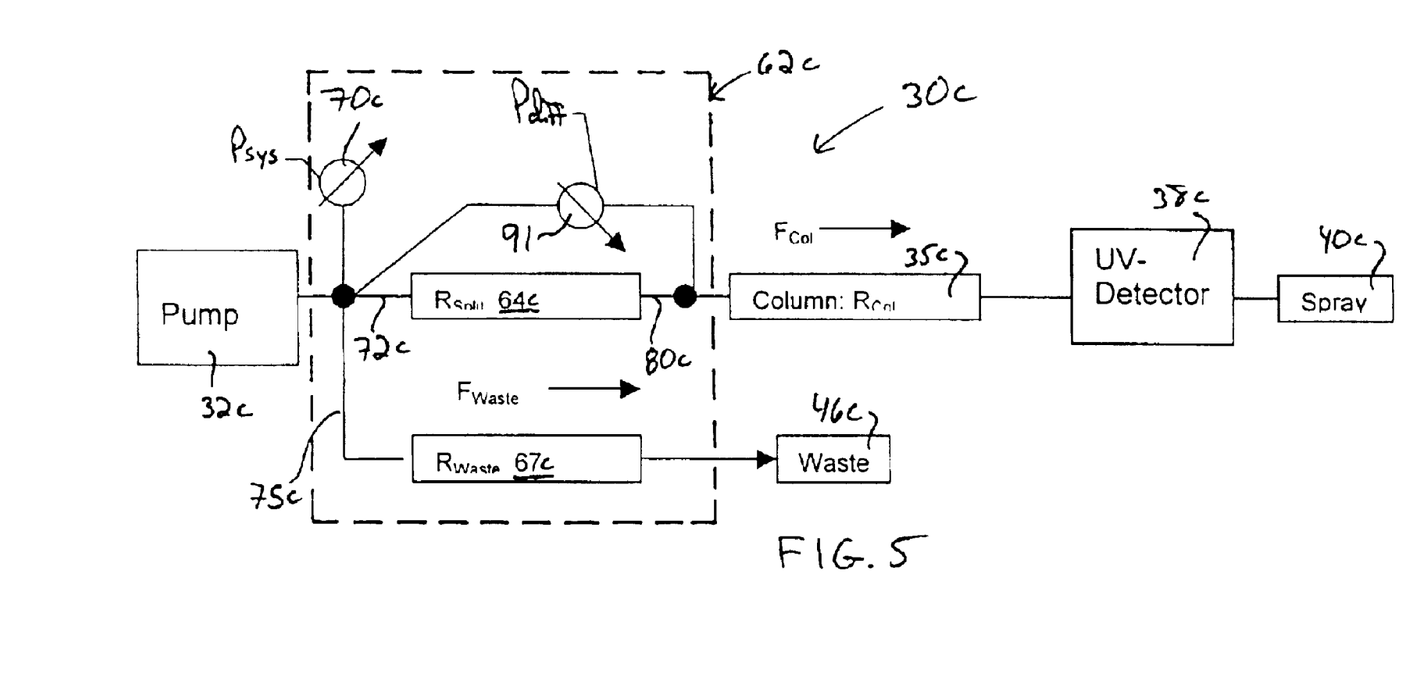
FIG. 5 is a schematic view of another apparatus for fluid control in accordance with the present invention.

In another embodiment of the present invention, system 30c is similar to system 30a described above but includes a flow control apparatus 62c having a differential pressure sensor 91 as shown in FIG. 5. Like reference numerals have been used to describe like components of system 30a and 30c.

In accordance with the present invention, flow control apparatus 62c includes a first pressure sensor 70c located before column capillary 64c and waste capillary 67c for measuring the system fluid pressure before the split in the same manner as discussed above.

Flow control apparatus also includes differential pressure sensor 91 which measures the differential pressure over column capillary 64c, that is, the difference in the upstream pressure in eluent supply line 72c before the column capillary and the downstream pressure in eluent feed line 80c after the column capillary.

Differential pressure sensor 91 allows monitoring of the pressure drop through column capillary 64c with high accuracy. With reference to FIG. 5, system fluid pressure sensor 70c monitors system fluid pressure $P_{sys}$ before the splitter and differential pressure sensor 91 monitors the differential in pressure $P_{diff}$ over column capillary 64c.

It is important to observe that instead of measuring the column and the system fluid pressure and then computing the difference (i.e., $P_{diff}=P_{sys}-P_{col}$) as in the above embodiments, this embodiment measures the differential pressure $P_{diff}$ directly by mounting differential pressure sensor in parallel to splitter capillary 64c and utilizing the fluid dynamic analogy to an ammeter, where column capillary 64c is the "shunt" resistor.

In operation and use, system 30c is used in substantially the same manner as 30a discussed above, except that the differential in pressure need not be calculated to determine quotient Q as the differential in pressure is measured directly by differential pressure sensor 91. Accordingly, quotient Q can be determined as follows:

$$Q=P_{sys}/P_{diff} \qquad \text{Eq. (t)}$$

where $P_{sys}$ is the system fluid pressure measured by system fluid pressure sensor 70c and $P_{diff}$ is the differential pressure measured by differential pressure sensor 91.

In many respects the modifications of the various figures resemble those of preceding modifications and the same reference numerals followed by subscript a, b and c designate corresponding parts.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

What is claimed is:

1. An apparatus for monitoring flow within a high pressure liquid chromatography system, said apparatus comprising:
   a pump for supplying a system flow of eluent to the system;
   a chromatography column;
   a flow splitting device including a first restrictor and a second restrictor, said first restrictor fluidly connecting said pump and said chromatography column and said second restrictor fluidly connecting said pump to a waste line;
   a first fluid pressure sensor monitoring a system fluid pressure upstream of said first restrictor;
   a second fluid pressure sensor monitoring a column fluid pressure downstream of said first restrictor; and
   a calculating device for calculating a quotient Q based upon said system fluid pressure and said column fluid pressure.

2. The apparatus of claim 1 further comprising:
   a supply line fluidly connecting said pump to said splitting device; and
   a feed line fluidly connecting said first restrictor to said column;
   wherein said first fluid pressure sensor coupled to said supply line for monitoring said system fluid pressure and said second fluid pressure sensor is coupled to said feed line for monitoring said column fluid pressure.

3. The apparatus of claim 1 wherein said calculating device calculates said quotient Q based upon said system fluid pressure and said column fluid pressure as follows:

$$Q=P_{sys}/(P_{sys}-P_{col})$$

wherein $P_{sys}$ is said system fluid pressure and $P_{col}$ is said column fluid pressure.

4. The apparatus of claim 3 further comprising a regulating device for regulating a required system flow $F_{sys}$ necessary to provide a desired column flow $F_{col}$ as follows:

$$F_{sys}=F_{col} \times S \times Q$$

wherein $F_{col}$ is the desired column flow, S is the split ratio of said flow splitting device, and Q is said quotient.

5. The apparatus of claim 3 further comprising a regulating device for regulating a required system flow $F_{sys}$ necessary to provide a desired column flow $F_{col}$ as follows:

$$F_{sys}=F_{col} \times (1+S \times Q)$$

wherein $F_{col}$ is the desired column flow, S is the split ratio of said flow splitting device, and Q is said quotient.

6. The apparatus of claim 3 further comprising a regulating device for regulating a required system flow $F_{sys}$ necessary to provide a desired column flow $F_{col}$ as follows:

$$F_{sys}=F_{col} \times S \times Q$$

wherein $F_{col}$ is the desired column flow, S is the split ratio of said flow splitting device, and Q is said quotient.

7. The apparatus of claim 1 further comprising a regulating device for regulating a required system flow necessary to provide a desired column flow based upon said system fluid pressure and said column fluid pressure.

8. An apparatus for monitoring flow within a high pressure liquid chromatography system, said apparatus comprising:
   a pump for supplying a system flow of eluent to the system;
   a chromatography column;
   a flow splitting device including a first restrictor and a second restrictor, said first restrictor fluidly connecting said pump and said chromatography column and said second restrictor fluidly connecting said pump to a waste line;
   a first fluid pressure sensor monitoring a system fluid pressure upstream of said first restrictor; and
   a differential fluid pressure sensor monitoring a pressure differential between said system fluid pressure and a column fluid pressure downstream of said first restrictor.

9. The apparatus of claim 8 further comprising a calculating device for calculating a quotient Q based upon said system fluid pressure and said pressure differential as follows:

$$Q=P_{sys}/P_{diff}$$

wherein $P_{sys}$ is said system fluid pressure and $P_{diff}$ is said pressure differential.

10. The apparatus of claim 9 further comprising a regulating device for regulating a required system flow $F_{sys}$ necessary to provide a desired column flow $F_{col}$ as follows:

$$F_{sys}=F_{col}\times(1+S)\times Q$$

wherein $F_{col}$ is the desired column flow, S is the split ratio of said flow splitting device, and Q is said quotient.

11. The apparatus of claim 9 further comprising a regulating device for regulating a required system flow $F_{sys}$ necessary to provide a desired column flow $F_{col}$ as follows:

$$F_{sys}=F_{col}\times(1+S\times Q)$$

wherein $F_{col}$ is the desired column flow, S is the split ratio of said flow splitting device, and Q is said quotient.

12. The apparatus of claim 9 further comprising a regulating device for regulating a required system flow $F_{sys}$ necessary to provide a desired column flow $F_{col}$ as follows:

$$F_{sys}=F_{col}\times S\times Q$$

wherein $F_{col}$ is the desired column flow, S is the split ratio of said flow splitting device, and Q is said quotient.

13. A method for regulating a desired column flow within a high pressure liquid chromatography system comprising the steps of:
  supplying an eluent via a supply line to a flow splitting device at a system flow rate;
  distributing said eluent from said splitting device via a feed line to a chromatography column;
  monitoring a system fluid pressure in said supply line;
  monitoring a column fluid pressure in said feed line; and
  calculating a quotient Q based upon said system fluid pressure and said column fluid pressure.

14. The method of claim 13 wherein said calculating step is accomplished by calculating said quotient Q as follows:

$$Q=P_{sys}/(P_{sys}-P_{col})$$

wherein $P_{sys}$ is said system fluid pressure and $P_{col}$ is said column fluid pressure.

15. The method of claim 14 further comprising the step of regulating a required system flow based upon quotient Q.

16. The method of claim 14 wherein said regulating step is accomplished by regulating said required system flow $F_{sys}$ as follows:

$$F_{sys}=F_{col}\times(1+S)\times Q$$

wherein $F_{col}$ is the desired column flow, S is the split ratio of said flow splitting device, and Q is said quotient.

17. The method of claim 14 wherein said regulating step is accomplished by regulating said required system flow $F_{sys}$ as follows:

$$F_{sys}=F_{col}\times(1+S\times Q)$$

wherein $F_{col}$ is the desired column flow, S is the split ratio of said flow splitting device, and Q is said quotient.

18. The method of claim 14 wherein said regulating step is accomplished by regulating said required system flow $F_{sys}$ as follows:

$$F_{sys}=F_{col}\times S\times Q$$

wherein $F_{col}$ is the desired column flow, S is the split ratio of said flow splitting device, and Q is said quotient.

19. The method of claim 13 wherein said calculating step is accomplished by calculating said quotient Q as follows:

$$Q=P_{sys}/P_{diff}$$

wherein $P_{sys}$ is said system fluid pressure and $P_{diff}$ is the differential pressure between said system fluid pressure and said column fluid pressure.

20. The method of claim 19 further comprising the step of regulating a required system flow based upon quotient Q.

21. The method of claim 19 wherein said regulating step is accomplished by regulating said required system flow $F_{sys}$ as follows:

$$F_{sys}=F_{col}\times(1+S)\times Q$$

wherein $F_{col}$ is the desired column flow, S is the split ratio of said flow splitting device, and Q is said quotient.

22. The method of claim 19 wherein said regulating step is accomplished by regulating said required system flow $F_{sys}$ as follows:

$$F_{sys}=F_{col}\times(1+S\times Q)$$

wherein $F_{col}$ is the desired column flow, S is the split ratio of said flow splitting device, and Q is said quotient.

23. The method of claim 19 wherein said regulating step is accomplished by regulating said required system flow $F_{sys}$ as follows:

$$F_{sys}=F_{col}\times S\times Q$$

wherein $F_{col}$ is the desired column flow, S is the split ratio of said flow splitting device, and Q is said quotient.

24. The method of claim 13 further comprising the step of adjusting said system flow rate to provide said desired column flow rate.

* * * * *